US012447335B2

(12) United States Patent
Park et al.

(10) Patent No.: US 12,447,335 B2
(45) Date of Patent: Oct. 21, 2025

(54) HAND PIECE FOR SKIN TREATMENT APPARATUS

(71) Applicant: VIOL CO., LTD., Seongnam-si (KR)

(72) Inventors: Yong Seok Park, Seoul (KR); Suji Lee, Seongnam-si (KR)

(73) Assignee: VIOL CO., LTD., Seongnam-si (KR)

( * ) Notice: Subject to any disclaimer, the term of this patent is extended or adjusted under 35 U.S.C. 154(b) by 0 days.

(21) Appl. No.: 18/713,270

(22) PCT Filed: Jun. 27, 2023

(86) PCT No.: PCT/KR2023/008978

§ 371 (c)(1),
(2) Date: May 24, 2024

(87) PCT Pub. No.: WO2024/005519

PCT Pub. Date: Jan. 4, 2024

(65) Prior Publication Data

US 2025/0121183 A1 Apr. 17, 2025

(30) Foreign Application Priority Data

Jun. 30, 2022 (KR) ........................ 10-2022-0080906

(51) Int. Cl.
*A61N 1/08* (2006.01)
*A61N 1/20* (2006.01)
(Continued)

(52) U.S. Cl.
CPC ............... *A61N 1/08* (2013.01); *A61N 1/205* (2013.01); *A61N 1/40* (2013.01); *A61N 7/00* (2013.01); *A61N 2007/0034* (2013.01)

(58) Field of Classification Search
CPC . A61N 1/08; A61N 1/205; A61N 1/40; A61N 7/00; A61N 2007/0034; A61H 7/00; A61H 37/00; A61H 2201/0153; A61H 2201/0188; A61H 2201/50; A61H 2201/5023; A61H 2201/5043; A61H 2201/5071; A61H 7/003
See application file for complete search history.

(56) References Cited

U.S. PATENT DOCUMENTS 7,771,374 B2 * 8/2010 Slatkine ................ A61M 5/425 601/7
2005/0251117 A1 * 11/2005 Anderson ............ A61B 18/203 606/41
(Continued)

FOREIGN PATENT DOCUMENTS

JP 2020-110621 7/2020
KR 10-2001-0110838 12/2001
(Continued)

*Primary Examiner* — Baisakhi Roy
(74) *Attorney, Agent, or Firm* — LEX IP MEISTER, PLLC

(57) ABSTRACT

Provided is a hand piece for a skin treatment apparatus, the hand piece including: a hand piece body capable of being operated by a user hand; a skin treatment unit connected to an end of the hand piece body, and treating a user skin; a pressure sensing unit installed on the skin treatment unit, and sensing a pressure between the skin and the skin treatment unit; and a pressure display unit emitting light in a plurality of colors based on a pressure value measured by the pressure sensing unit.

5 Claims, 7 Drawing Sheets

(51) Int. Cl.
*A61N 1/40* (2006.01)
*A61N 7/00* (2006.01)

(56) References Cited

U.S. PATENT DOCUMENTS

2006/0259102 A1* 11/2006 Slatkine ............... A61B 17/205 607/88
2010/0063565 A1* 3/2010 Beerwerth ........... A61B 18/203 607/88
2012/0226306 A1* 9/2012 Jackson .............. A61F 13/0259 606/201
2013/0245727 A1* 9/2013 Kothare ................. A61N 1/328 607/101
2014/0202493 A1* 7/2014 Zelickson .............. B23Q 5/046 134/6
2019/0224478 A1* 7/2019 Yoon ...................... A61N 1/328
2023/0065052 A1* 3/2023 Kim ........................ A61N 1/328
2023/0149260 A1* 5/2023 Popovici ................ A61H 39/04 606/204
2023/0172799 A1* 6/2023 Black ..................... A61H 23/02 601/84
2023/0200811 A1* 6/2023 Black ................... A61B 17/072 227/175.1
2024/0366970 A1* 11/2024 Li ............................ A61N 7/02
2024/0389986 A1* 11/2024 Harden .................. A61B 17/00

FOREIGN PATENT DOCUMENTS

KR 10-2007-0064883 6/2007
KR 2016-0099332 8/2016
KR 10-1984931 6/2019
KR 10-2260212 6/2021
KR 10-2022-0010777 1/2022
KR 10-2022-0043160 4/2022

* cited by examiner

HAND PIECE FOR SKIN TREATMENT APPARATUS

TECHNICAL FIELD

The present disclosure relates to a hand piece for a skin treatment apparatus, and more particularly, to a hand piece for a skin treatment apparatus that allows a user to visually check a pressure transmitted to a skin.

BACKGROUND ART

In recent years, a home skin treatment apparatus has been developed for skin care or obesity treatment, the home skin treatment apparatus having various functions enabling such as a high intensity focused ultrasound (HIFU) procedure, a radio frequency (RF) procedure, a galvanization procedure, and an ultrasound procedure. Most users of the home skin treatment apparatus are non-experts, and the home skin treatment apparatus may thus have an energy output value set to be significantly lower than that of a hospital skin treatment apparatus. The home skin treatment apparatus may thus be required to be in contact with a user skin while having accurate pressure and inclination for the user to expect an actual treatment effect.

The hospital skin treatment apparatus may also be required to maintain a predetermined pressure to increase the treatment effect when performing a non-invasive procedure that requires a rubbing motion. However, the hospital skin treatment apparatus may depend on the sensation or experience of a procedure operator. Therefore, friction of irregular intensity, temperature, or pressure may damage the skin, thereby providing a route for viral infection.

DISCLOSURE

Technical Problem

The present disclosure attempts to provide a hand piece for a skin treatment apparatus that always performs a procedure at an optimal pressure regardless of the sensation or experience of a procedure operator or user by allowing the user to visually check a pressure.

Technical Solution

According to an embodiment, provided is a hand piece for a skin treatment apparatus, the hand piece including: a hand piece body capable of being operated by a user hand; a skin treatment unit connected to an end of the hand piece body, and treating a user skin; a pressure sensing unit installed on the skin treatment unit, and sensing a pressure between the skin and the skin treatment unit; and a pressure display unit emitting light in a plurality of colors based on a pressure value measured by the pressure sensing unit.

The pressure sensing unit may include the plurality of pressure sensors installed on a plurality of points of the skin treatment unit and measuring the plurality of pressure values.

A plurality of pressure sensors may be disposed at the same distance along an edge of a front end surface of the skin treatment unit.

The pressure display unit may emit light in the plurality of colors based on the plurality of pressure values measured by the plurality of pressure sensors and a deviation between the plurality of pressure values.

The hand piece may further include a control unit controlling the pressure display unit by transmitting, to the pressure display unit, a control signal based on the plurality of pressure values measured by the plurality of pressure sensors and the deviation between the plurality of pressure values.

The pressure sensing unit may include a plurality of elastic assemblies installed between the hand piece body and the skin treatment unit, and each having a length changed based on the pressure at which the skin treatment unit presses the skin.

The elastic assembly may include multi-stage pogo pins each mounted with an elastic body having a different elastic modulus for each stage.

The multi-stage pogo pins may include an upper pogo pin adjacent to the skin treatment unit, a lower pogo pin adjacent to the hand piece body, and an intermediate pogo pin disposed between the upper pogo pin and the lower pogo pin, and the elastic modulus of the elastic body mounted on each of the upper pogo pin, the intermediate pogo pin, and the lower pogo pin may be increased from the upper pogo pin to the lower pogo pin.

The elastic modulus of the upper elastic body mounted on the upper pogo pin may be below a predetermined pressure reference range, the elastic modulus of the intermediate elastic body mounted on the intermediate pogo pin may be within the pressure reference range, and the elastic modulus of the lower elastic body mounted on the lower pogo pin may be above the pressure reference range.

The pressure display unit may emit light in the plurality of colors as the length of the elastic assembly is changed.

The hand piece may further include a control unit controlling the pressure display unit by transmitting, to the pressure display unit, a control signal based on a length change of the elastic assembly.

Advantageous Effects

As set forth above, the hand piece for a skin treatment apparatus according to an embodiment of the present disclosure may always perform the procedure at the optimal pressure regardless of the sensation or experience of the procedure operator or user by allowing the procedure operator or user to use the pressure display unit to thus visually check the pressure on the user skin.

In addition, the hand piece for a skin treatment apparatus according to an embodiment of the present disclosure may maximize the procedure effect by allowing the procedure operator or user to check the pressure or the deviation, displayed on the pressure display unit, and adjust the pressure or the deviation on the user skin in real time.

In addition, the hand piece for a skin treatment apparatus according to an embodiment of the present disclosure may have the improved product reliability by allowing the procedure operator or user to immediately check the safety on the skin.

MODE FOR INVENTION

Hereinafter, embodiments of the present disclosure are described in detail with reference to the accompanying drawings so that those skilled in the art to which the present disclosure pertains may easily practice the present disclosure. The present disclosure may be implemented in various different forms and is not limited to the embodiments provided herein.

Figure 1:
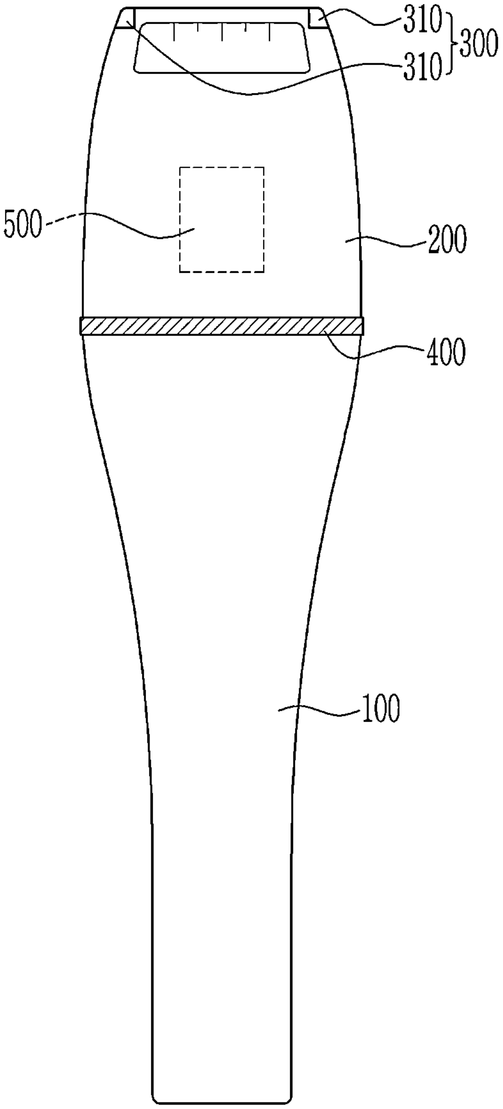
FIG. 1 is a schematic plan view of a hand piece for a skin treatment apparatus according to an embodiment of the present disclosure.

FIG. 1 is a schematic plan view of a hand piece for a skin treatment apparatus according to an embodiment of the present disclosure.

As shown in FIG. 1, a hand piece for a skin treatment apparatus according to an embodiment of the present disclosure may include a hand piece body 100, a skin treatment unit 200, a pressure sensing unit 300, a pressure display unit 400, and a control unit 500.

The hand piece body 100 may usually have a modified cylindrical shape to be easily held by a user hand, is not necessarily limited thereto, and have various shapes.

The skin treatment unit 200 may be connected to an end of the hand piece body 100, and may treat a user skin. The skin treatment unit 200 may include a sharp needle-shaped needle part, is not necessarily limited thereto, and may have various structures as long as the skin treatment unit may treat the skin. That is, the skin treatment unit 200 may have a structure enabling a high intensity focused ultrasound (HIFU) procedure, a galvanic procedure, a non-invasive procedure, an invasive radio frequency (RF) procedure, or the like.

The pressure sensing unit 300 may be installed on the skin treatment unit 200, and sense a pressure between a user skin S and the skin treatment unit 200.

The pressure sensing unit 300 may include a plurality of pressure sensors 310 installed on a plurality of points of the skin treatment unit 200, and measuring a plurality of pressure values.

Figure 2:
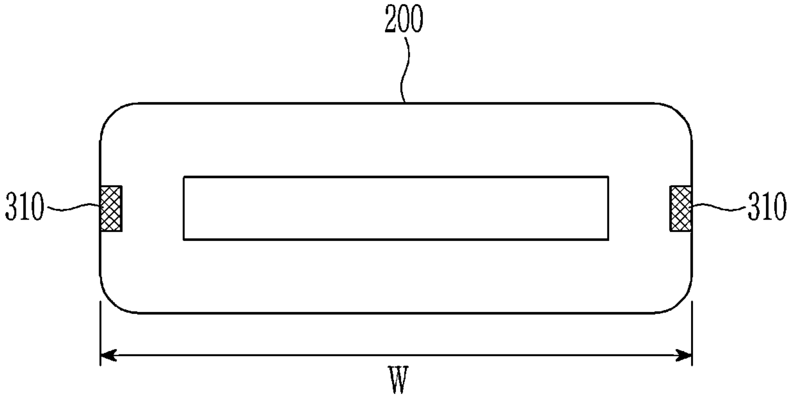
FIG. 2 is a view showing an arrangement structure of a plurality of pressure sensors according to an embodiment.
Figure 3:
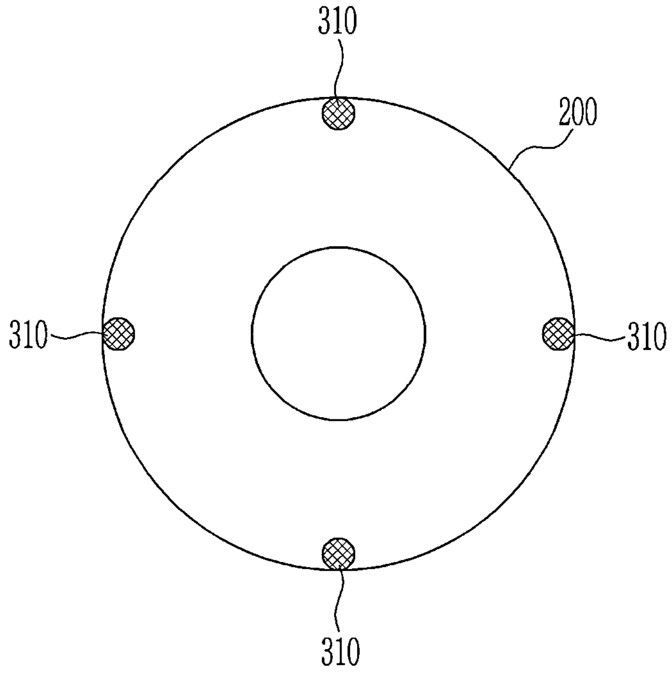
FIG. 3 is a view showing an arrangement structure of the plurality of pressure sensors according to another embodiment.

FIG. 2 is a view showing an arrangement structure of the plurality of pressure sensors according to an embodiment, and FIG. 3 is a view showing an arrangement structure of the plurality of pressure sensors according to another embodiment.

As shown in FIGS. 2 and 3, the plurality of pressure sensors 310 may be at least two sensors, and arranged on a front-end surface of the skin treatment unit 200. The plurality of pressure sensors 310 may be disposed at the same distance along an edge of the front-end surface of the skin treatment unit 200.

As shown in FIG. 2, the two pressure sensors 310 in an embodiment may be disposed at the same distance along the edge of the front-end surface of the skin treatment unit 200. Here, the two pressure sensors 310 may be disposed to be spaced apart from each other at the maximum distance in a width direction W of the front-end surface of the skin treatment unit 200.

Alternatively, as shown in FIG. 3, the four pressure sensors 310 in another embodiment may be arranged at the same distance along the edge of the front-end surface of the skin treatment unit 200. Here, the four pressure sensors 310 may be disposed to be spaced apart from each other at the maximum along the edge of the front-end surface of the skin treatment unit 200.

As described above, the plurality of pressure sensors 310 may be disposed at the same distance along the edge of the front-end surface of the skin treatment unit 200, thereby preventing the hand piece for a skin treatment apparatus according to an embodiment of the present disclosure from being tilted to one side or preventing the pressure from being measured while a portion of the front-end surface of the skin treatment unit 200 is separated from the skin S. Therefore, the hand piece according to an embodiment of the present disclosure may more accurately sense the pressure between the skin S and the skin treatment unit 200.

The embodiments shown in FIGS. 2 and 3 describe the respective arrangement structures of the two and four pressure sensors, and are not necessarily limited thereto. However, the arrangement structure of the plurality of pressure sensors 310 may be changed in various ways and applied for more accurate pressure measurement.

The pressure display unit 400 may emit light in a plurality of colors based on the pressure value measured by the pressure sensing unit 300. In detail, the pressure display unit 400 may emit light in the plurality of colors based on the plurality of pressure values measured by the plurality of pressure sensors 310 and a deviation between the plurality of pressure values. The pressure display unit 400 may include a light emitting diode (LED).

The control unit 500 may control the pressure display unit 400 by transmitting, to the pressure display unit 400, a control signal based on the plurality of pressure values measured by the plurality of pressure sensors 310 and the deviation between the plurality of pressure values.

Figure 4:
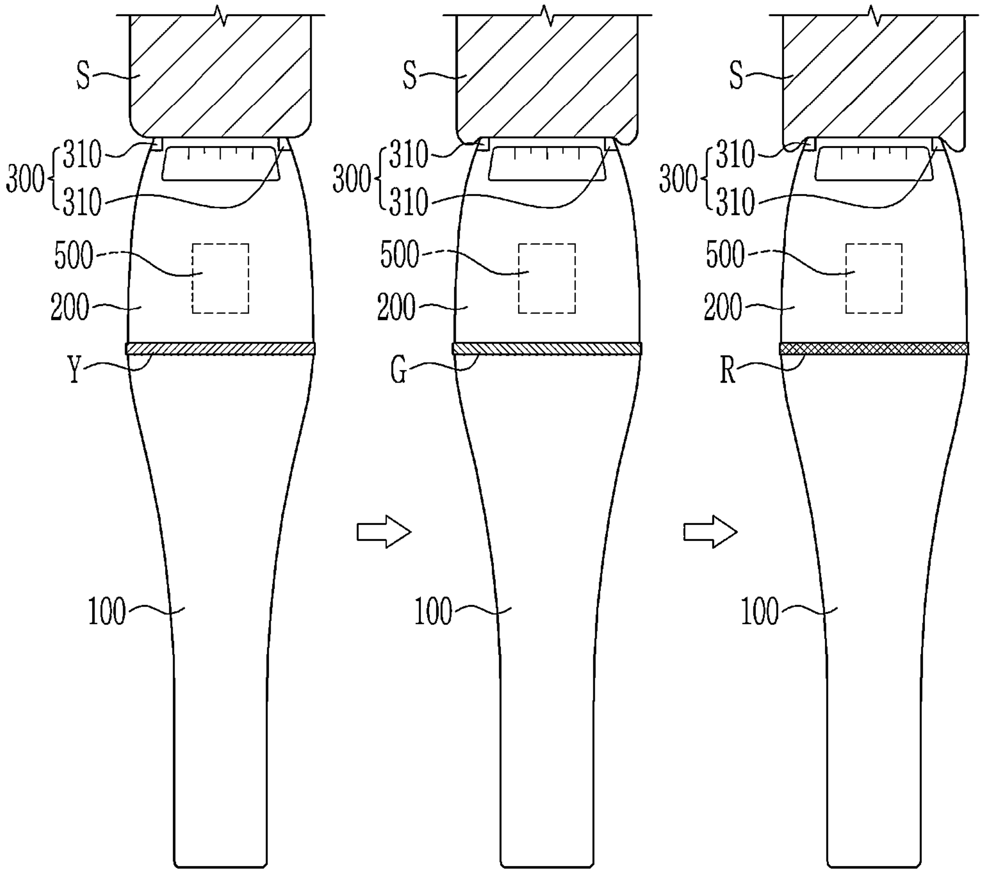
FIG. 4 is a view showing a color change of a pressure display unit, based on a pressure at which the hand piece for a skin treatment apparatus presses a user skin according to an embodiment of the present disclosure.

FIG. 4 is a view showing the color change of the pressure display unit, based on the pressure at which the hand piece for a skin treatment apparatus presses the user skin according to an embodiment of the present disclosure.

As shown in FIG. 4, the hand piece for a skin treatment apparatus according to an embodiment of the present disclosure may increase the pressure on the user skin S, and the color of the pressure display unit 400 may thus be changed to yellow Y, green G, or red R. When the color of the pressure display unit 400 is the yellow Y, this color may display that the pressure or the deviation is below its reference range; when the color of the pressure display unit 400 is the green G, this color may display that the pressure or the deviation satisfies the reference range; and when the color of the pressure display unit 400 is the red R, this color may display that the pressure or the deviation is above the reference range.

In this embodiment, the colors of the pressure display unit 400 is changed to yellow (Y), green (G), and red (R), are not necessarily limited thereto, and changed to various colors to thus display a pressure change.

In this way, the hand piece for a skin treatment apparatus according to an embodiment of the present disclosure may always perform its procedure at the optimal pressure regardless of the sensation or experience of a procedure operator or the user by allowing the user to use the pressure display unit to thus visually check the pressure or the deviation on the skin.

That is, the hand piece for a skin treatment apparatus according to an embodiment of the present disclosure may maximize a procedure effect by allowing the procedure operator or user to check the pressure or the deviation, displayed on the pressure display unit, and adjust the pressure or the deviation on the skin in real time.

In addition, the hand piece for a skin treatment apparatus according to an embodiment of the present disclosure may have improved product reliability by allowing the procedure operator or user to immediately check safety on the skin.

Meanwhile, the pressure sensing unit in this embodiment includes the plurality of pressure sensors, and a pressure sensing unit in another embodiment may include an elastic assembly.

Hereinafter, the description describes a hand piece for a skin treatment apparatus according to another embodiment of the present disclosure in detail with reference to FIGS. 5 to 7.

Figure 5:
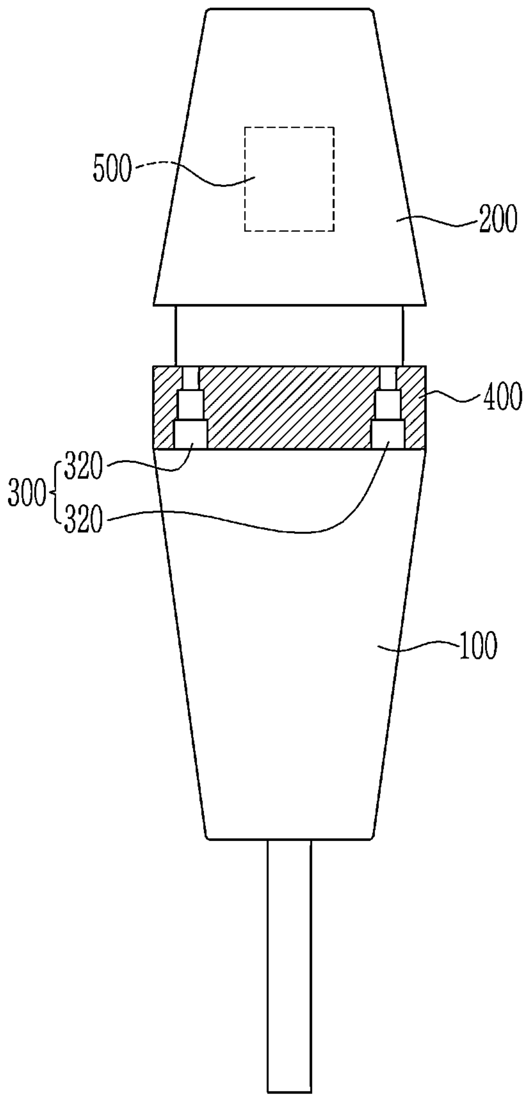
FIG. 5 is a schematic plan view of the hand piece for a skin treatment apparatus according to another embodiment of the present disclosure.

FIG. 5 is a schematic plan view of the hand piece for a skin treatment apparatus according to another embodiment of the present disclosure.

Another embodiment shown in FIG. 5 is substantially the same as an embodiment shown in FIG. 1 except for a structure of the pressure sensing unit, and the description thus omits redundant descriptions thereof.

As shown in FIG. 5, the hand piece for a skin treatment apparatus according to another embodiment of the present disclosure may include the hand piece body 100, the skin treatment unit 200, the pressure sensing unit 300, the pressure display unit 400, and the control unit 500.

The pressure sensing unit 300 may be installed between the hand piece body 100 and the skin treatment unit 200. The pressure sensing unit 300 may include a plurality of elastic assemblies 320 each having a length changed based on the pressure at which the skin treatment unit 200 presses the skin S. One elastic assembly 320 may include multi-stage pogo pins each mounted with an elastic body 32 having a different elastic modulus for each stage. Hereinafter, the description describes the elastic assembly 320 by using the multi-stage pogo pins as its example.

Figure 6:
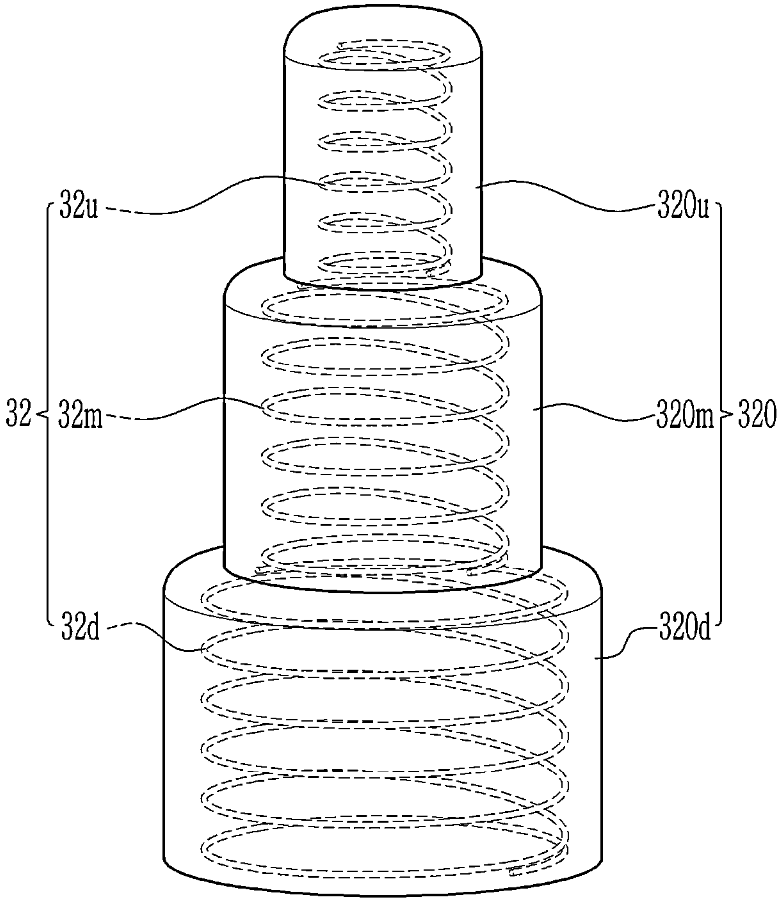
FIG. 6 is a detailed perspective view of an elastic assembly of FIG. 5.

FIG. 6 is a detailed perspective view of the elastic assembly of FIG. 5.

As shown in FIG. 6, the multi-stage pogo pins 320 may include an upper pogo pin 320*u* adjacent to the skin treatment unit 200, a lower pogo pin 320*d* adjacent to the hand piece body 100, and an intermediate pogo pin 320*m* disposed between the upper pogo pin 320*u* and the lower pogo pin 320*d*.

Here, the elastic modulus of the elastic body 32 mounted on each of the upper pogo pin 320*u*, the intermediate pogo pin 320*m*, and the lower pogo pin 320*d* may be increased from the upper pogo pin 320*u*, to the intermediate pogo pin 320*m*, and to the lower pogo pin 320*d*. Each elastic modulus of elastic bodies 32*u*, 32*m*, 32*d* each mounted on the upper pogo pin 320*u*, the intermediate pogo pin 320*m*, and the lower pogo pin 320*d* may correspond to a predetermined pressure reference.

That is, the elastic modulus of the upper elastic body 32*u* mounted on the upper pogo pin 320*u* may be below a predetermined pressure reference range, the elastic modulus of the elastic body 32*m* mounted on the intermediate pogo pin 320*m* may be within the pressure reference range, and the elastic modulus of the lower elastic body 32*d* mounted on the lower pogo pin 320*d* may be above the pressure reference range.

The pressure display unit 400 may emit light in the plurality of colors as a length L of the elastic assembly 320 is changed. The pressure display unit 400 may include the light emitting diode (LED).

The control unit 500 may control the pressure display unit 400 by transmitting, to the pressure display unit 400, a control signal based on a length change of the elastic assembly.

Figure 7:
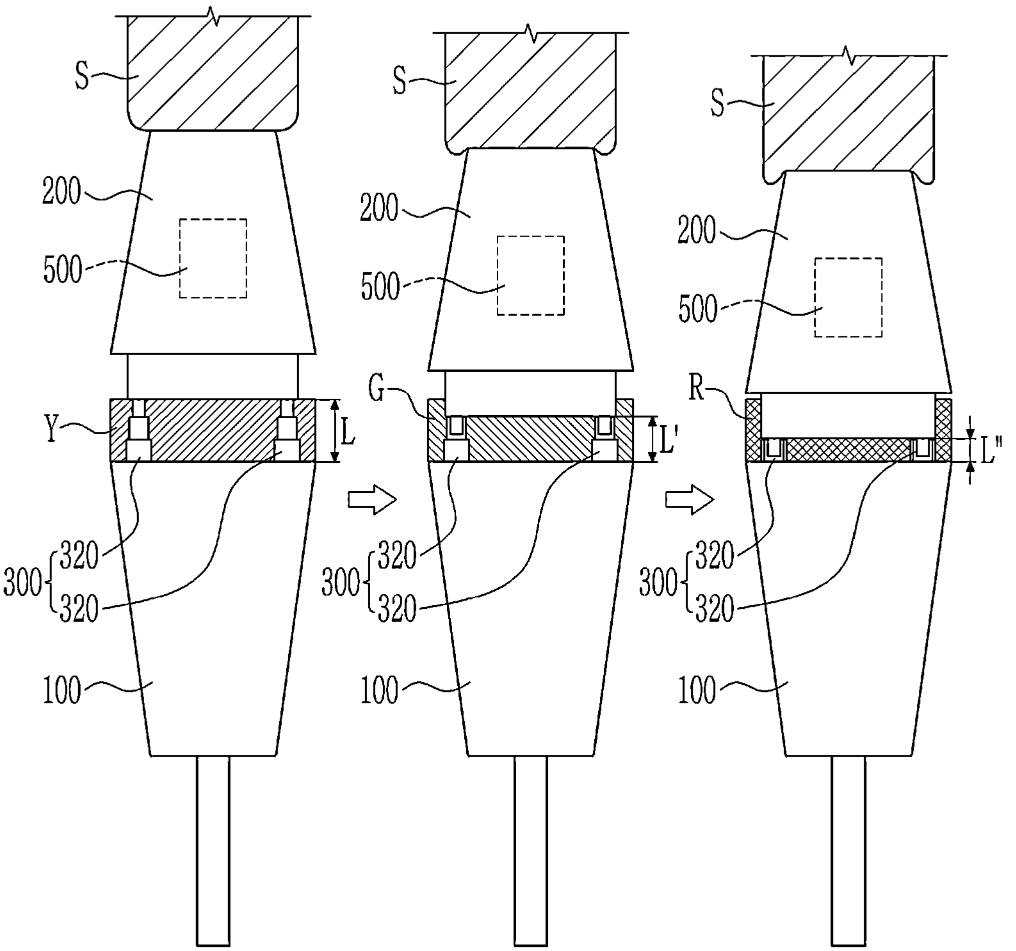
FIG. 7 is a view showing a color change of the pressure display unit, based on the pressure at which the hand piece for a skin treatment apparatus presses the user skin according to another embodiment of the present disclosure.

FIG. 7 is a view showing a color change of the pressure display unit, based on the pressure at which the hand piece for a skin treatment apparatus presses the user skin according to another embodiment of the present disclosure.

As shown in FIG. 7, the hand piece for a skin treatment apparatus according to another embodiment of the present disclosure may increase the pressure on the user skin S, and the length of the elastic assembly 320 may be changed from L, to L', and to L". In response thereto, the color of the pressure display unit 400 may also be changed to the yellow Y, the green G, or the red R. When the color of the pressure display unit 400 is the yellow Y, this color may display that the pressure or the deviation is below the pressure reference range; when the color of the pressure display unit 400 is the green G, this color may display that the pressure or the deviation satisfies the pressure reference range; and when the color of the pressure display unit 400 is the red R, this color may display that the pressure or the deviation is above the pressure reference range.

Although the embodiments of the present disclosure have been described above, the present disclosure is not limited thereto. It is apparent to those skilled in the art to which the present disclosure pertains that the present disclosure may be variously modified and altered without departing from the spirit and scope of the present disclosure claimed in the appended claims.

<Description of symbols>

| | |
|---|---|
| 100: hand piece body | 200: skin treatment unit |
| 300: pressure sensing unit | 400: pressure display unit |
| 500: control unit | |

The invention claimed is:

1. A hand piece for a skin treatment apparatus, the hand piece comprising:

a hand piece body capable of being operated by a user hand;

a skin treatment unit connected to an end of the hand piece body, and treating a user skin;

a pressure sensing unit installed on the skin treatment unit, and sensing a pressure between the skin and the skin treatment unit; and a pressure display unit emitting light in a plurality of colors corresponding to respective ranges of on a pressure value measured by the pressure sensing unit, wherein the pressure sensing unit includes a plurality of elastic assemblies change in length in response to the pressure at which the skin treatment unit presses on the skin, wherein the elastic assembly includes an upper elastic body adjacent to the skin treatment unit, a lower elastic body adjacent to the hand piece body, and an intermediate elastic body disposed between the upper elastic body and the lower elastic body, and wherein an elastic modulus of the intermediate elastic body is within a predetermined pressure reference range, an elastic modulus of the upper elastic body is below the predetermined pressure reference range, and an elastic modulus of the lower elastic body is above the predetermined pressure reference range.

2. The hand piece of claim 1, wherein the plurality of elastic assemblies are installed between the hand piece body and the skin treatment unit.

3. The hand piece of claim 2, wherein the elastic assembly includes a multi-stage pogo pin including an upper pogo pin adjacent to the skin treatment unit, a lower pogo pin adjacent to the hand piece body, and an intermediate pogo pin disposed between the upper pogo pin and the lower pogo pin, and the upper elastic body, the intermediate elastic body, and the lower elastic body are mounted on the upper pogo pin, the intermediate pogo pin, and the lower pogo pin, respectively.

4. The hand piece of claim 2, wherein the pressure display unit emits light in the plurality of colors as the length of the elastic assembly is changed.

5. The hand piece of claim 4, further comprising a control unit controlling the pressure display unit by transmitting, to the pressure display unit, a control signal in response to on a length change of the elastic assembly.

* * * * *